United States Patent [19]

Anthony et al.

[11] Patent Number: 5,525,479
[45] Date of Patent: Jun. 11, 1996

[54] FLUORESCENCE ASSAY OF RAS FARNESYL PROTEIN TRANSFERASE

[75] Inventors: Neville J. Anthony, Hatfield; David L. Pompliano, Lansdale, both of Pa.

[73] Assignee: Merck & Co., Inc., Rahway, N.J.

[21] Appl. No.: 199,778

[22] Filed: Feb. 17, 1994

Related U.S. Application Data

[63] Continuation-in-part of Ser. No. 899,400, Jun. 17, 1992, abandoned.

[51] Int. Cl.$^6$ .............................. C12Q 1/48; C12Q 1/00; A01N 37/18
[52] U.S. Cl. ......................... 435/15; 435/4; 514/2
[58] Field of Search ........................ 435/15, 4, 24, 435/18; 514/305, 2

[56] References Cited

U.S. PATENT DOCUMENTS

| | | | |
|---|---|---|---|
| 5,043,268 | 8/1991 | Stock | 435/15 |
| 5,135,935 | 8/1992 | Alberts et al. | 514/305 |
| 5,141,851 | 8/1992 | Brown et al. | 435/15 |

FOREIGN PATENT DOCUMENTS

| | | |
|---|---|---|
| 0456180A1 | 11/1991 | European Pat. Off. . |
| 0461869A2 | 12/1991 | European Pat. Off. . |
| WO91/16340 | 10/1991 | WIPO . |

OTHER PUBLICATIONS

Goldstein, J. L., et al., Nonfarnesylated Tetrapeptide Inhibitors of Protein Farnesyltransferase, (1991), Jour. of Biological Chemistry, 266, No. 24, pp. 15575–15578.

Schaber, M. D., et al., Polyisoprenylation of Ras in Vitro by a Farnesyl–Protein Transferase, (1990), Jour. Biol. Chemistry, 265, pp. 14701–14704.

Pompliano, D. L., et al., Intramolecular Fluorescence Enhancement: A Continuous Assay of Ras Farnesyl:Protein Transferase, (1992), J. Amer. Chem. Soc., 114, No. 20, pp. 7945–7946.

Reiss, Y., Purification of ras Farnesyl:Protein Transferase, (1990), Methods: A Companion to Methods in Enzymology, 1, No. 3, pp. 241–245.

*Primary Examiner*—Michael G. Wityshyn
*Assistant Examiner*—Louise N. Leary
*Attorney, Agent, or Firm*—David A. Muthard; Mark R. Daniel

[57] ABSTRACT

This invention is directed to a continuous fluorescence assay of Ras farnesyl:protein transferase. This assay can be used to screen for inhibitors of farnesyl:protein transferase. The assay may also be modified to screen for inhibitors of other protein transferases.

9 Claims, 1 Drawing Sheet

FLUORESCENCE ASSAY OF RAS FARNESYL PROTEIN TRANSFERASE

RELATED APPLICATIONS

This application is a continuation-in-part of application Ser. No. 07/899,400, filed Jun. 17, 1992, now abandoned.

BACKGROUND OF THE INVENTION

Posttranslational addition of hydrophobic moieties (fatty acid acylation and prenylation) is a functionally essential modification for many proteins involved in intracellular signalling pathways (Olsen, et al., *Biochemistry*, 29, 2623–2634 (1990); McIlhinney, et al., *J. Trends Biochem. Sci.*, 15, 387–391 (1990); Gordon, et al., *J. Biol. Chem.*, 266, 8647–8650 (1991); Glomset, et al., *Trends Biochem. Sci.*, 15, 139–142 (1990); Maltese, et al., *FASEB J.*, 4, 3319–3328 (1990); Rine, et al., *New Biologist*, 2, 219–226 (1990); Der, et al., *Cancer Cells* 3, 331–340, (1991); Sinensky, et al., *BioEssays*, 14, 25–31 (1992)).

Farnesyl:protein transferase (FPTase) catalyzes the transfer of a hydrophobic farnesyl group ($C_{15}$) from farnesyl diphosphate to a specific C-terminal cysteine residue of a protein substrate, forming a thioether bond and displacing inorganic pyrophosphate in the process (Manne, et al., *Proc. Natl. Acad, Sci. USA*, 87, 7541–7545 (1990); Schaber, et al., *J. Biol. Chem.*, 265, 14701–14704 (1990); Reiss, et al., *Cell*, 62, 81–88 (1990)). Short peptides ($\geq 4$ residues) containing a C-terminal consensus recognition sequence can also serve as farnesylation acceptor substates (Reiss, et al., *Cell*, 62, 81–88 (1990); Moores, et al., *J. Biol. Chem.*, 266, 14603–14610 (1991)). Interest in FPTase has intensified because farnesylation is required for membrane association and biological function of ras-encoded proteins (Willumsen, et al., *EMBO J.* 3, 2581–2585 (1984); Hancock, et al., *Cell*, 57, 1167–1177 (1989); Jackson, et al., *Proc. Natl. Acad. Sci. USA*, 87, 3042–3046 (1990)), mutant forms of which play a causitive role in over 20% of all human cancers, including greater than 50% of pancreatic and colon tumors (Bos, *Molecular Genetics in Cancer Diagnosis* (Cossman, J., Ed.), Elsevier Science Publishing Co., New York, pp 273–288 (1991)).

Inhibition of FPTase represents a possible method for preventing relocation of mutant Ras from the cytosol to the membrane, thereby blocking its cell transforming function. Enzymological studies and the search for potent, specific inhibitors led to consideration of alternatives to the existing stopped-point assays for FPTase activity, which are labor intensive and generate radioactive waste (Reiss, et al., *Methods: A Companion to Methods in Enzymology*, 1, 241–245 (1990)).

Study of the transferase enzymes that catalyze modifications for many proteins involved in intracellular signalling pathways has been hampered by troublesome stopped-point methods for assaying their activity. It is therefore an object of this invention to develop a continuous fluorescence assay for one of these enzymes, farnesyl:protein transferase. This assay utilizes a feature found in hydrophobic modification reactions which is the increase in hydrophobicity about the reaction center of the acceptor substrate that occurs following conversion of substrate to product. In comparison to the stopped point assays as found in the art, the assay of this invention is more accurate, less time-consuming, and does not produce radioactive waste.

BRIEF DESCRIPTION OF THE DRAWINGS

FIG. 1A is a fluorescence progress curve, A, of the reaction catalyzed by recombinant human farnesyl:protein transferase (hFPTase; 0.5 nM) using Ds-GlyCysValLeySer (SEQ.ID.NO.:1) (1.0 μM) as substrate in the presence of a saturating concentration of farnesyl diphosphate (10 mM) in assay buffer (50 mM Tris-HCl, pH 7.5, 5 mM DTT, 5 mM $MgCl_2$, 10 μM $ZnCl_2$, and 0.2% octyl-β-D-glucopyranoside) at 30° C. Fluorescence data in the integration mode were obtained on a SPEX Fluorolog Model F112X1 spectrofluorimeter with $\lambda_{ex}$=340 nm (slit width=4 nm) and $\lambda_{em}$=505 nm (slit width=8 nm) using 4 mm square microcells. Concentrations of stock solutions of Ds-GlyCysValLeuSer (SEQ.ID.NO.: 1 ) (in 20 mM Tris-CHl, pH 7.5, 10 mM EDTA) were calculated from the extinction coefficient of the dansyl moiety at 340 nm($\epsilon$=4250 $M^{-1}cm^{-1}$).

FIG. 1B: Fluorescence emission spectrum ($\lambda_{ex}$=340 nm) of: B, substrate Ds-GlyCysValLeuSer (SEQ.ID.NO.: 1 ) (1.0 μM in assay buffer), C, product Ds-GlyCysValLeuSer (1.0 μM in assay buffer), and D, difference between substrate and product.

FIG. 2 details inhibition of hFPTase by peptide CysIlePheMet (SEQ.ID.NO.:2). Double reciprocal plot of initial velocity versus Ds-GlyCysValLeuSer (SEQ.ID.NO.:1) concentration in the presence of (•)0, and () 50 nM CysIlePheMet (SEQ.ID.NO.:2) at 30° C. Reactions (400 μL) contained hFPTase(1 nM), FPP (10 μM) and varying concentrations of Ds-GlyCysValLeuSer (SEQ.ID.NO.:1) with or without 50 nM peptide CysIlePheMet (SEQ.ID.NO.:2) in assay buffer (see FIG. 1).

SUMMARY OF THE INVENTION

Figure 1A:
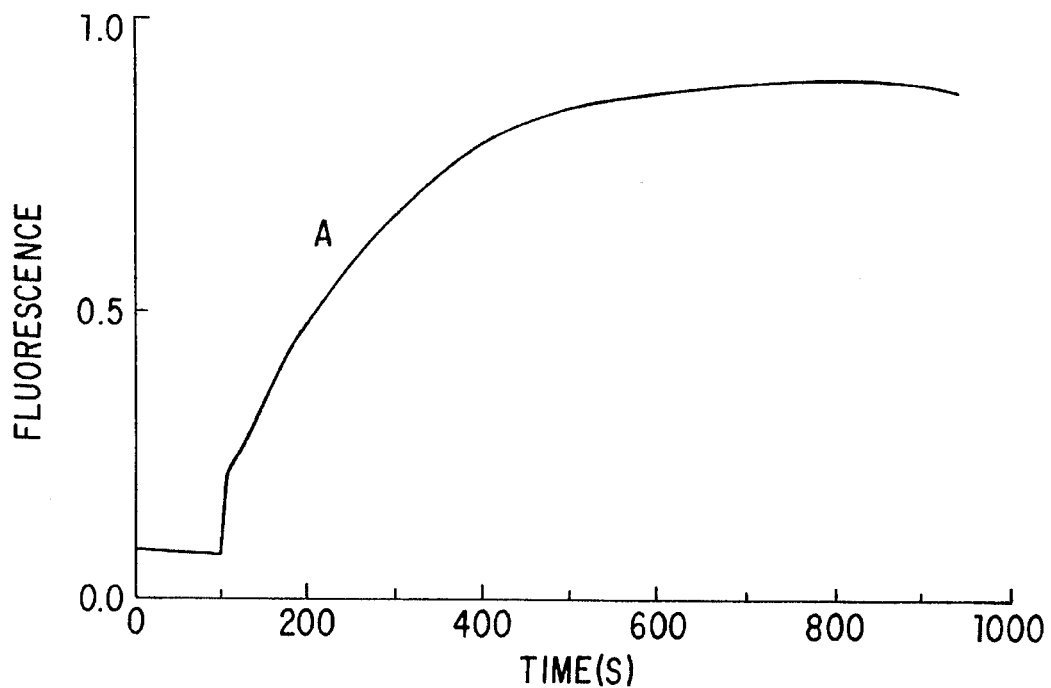
FIGS. 1A and 1B

The present invention is directed to a continuous fluorescence assay of Ras farnesyl:protein transferase. This assay can be used to screen for inhibitors of farnesyl:protein transferase. This assay utilizes a feature found in hydrophobic modification reactions which is the increase in hydrophobicity about the reaction center of the acceptor substrate that occurs following conversion of substrate to product.

DETAILED DESCRIPTION OF THE INVENTION

The present invention is directed to a continuous fluorescence assay of Ras farnesyl:protein transferase. This assay can be used to screen for inhibitors of farnesyl:protein transferase.

Generally the assay comprises the steps of:

(a) reacting an acceptor peptide substrate, wherein the acceptor peptide substrate has a fluorescence probe positioned proximally to the reaction center, with farnesyl diphosphate in the presence of a substance suspected of having farnesyl:protein transferase activity; and (b) detecting whether the farnesyl residue is incorporated into the protein or peptide substrate, in which incorporation of the farnesyl residue into the protein or peptide substrate indicates farnesyl:protein transferase activity.

In an embodiment of the assay of the instant invention the incorporation of the farnesyl residue is detected by an enhancement of the fluorescence of the reaction.

The continuous fluorescence assay monitors the progress of a transferase or ligase type of reaction, where the enhancement of fluorescence results from change in chemical environment caused by the covalent attachment of two substrates. Other continuous fluorescence assays have been devised for hydrolases or lyases (proteases, lipases, phosphatases, etc), where the reporter group changes it fluorescence properties after the parent substrate has been cleaved (Matayoshi, et al. *Science*, 247, 954–958 (1990); Garcia-Echeverria, et al., *J. Am. Chem. Soc.*, 114, 2758–2759 (1992); Shashidhar, et al., *Anal. Biochem.*, 198, 10–14, (1991)).

In addition to simplifying enzyme mechanistic studies, the assay, adapted to a 96-well plate format, will facilitate high volume drug screening efforts. Monitoring a product-associated change in the local molecular environment of a fluorescence reporter group should be applicable to other enzymes which change the hydrophobicity of their substrates, such as geranylgeranyl transferase (which along with farnesyl:protein transferase is known generally as a prenyl:protein transferase), and fatty acyl transferases such as palmitoyl and N-myristoyl transferases. For example, an assay for geranylgeranyl protein transferase activity would comprise geranylgeranyl protein transferase, an appropriate geranylgeranyl protein transferase acceptor peptide substrate which has a fluorescence probe positioned proximally to the reaction center, such as dansyl-GlyCysAlaIleLeu and the like, and geranylgeranyl diphosphate. An appropriate acceptor peptide substrate, which has a fluorescence probe positioned proximally to the reaction center, for assaying N-myristoyl transferase activity is, for example, GlyAsh(c-Ds-Lys) AlaAlaAlaArgArg (Towler, D. A. et al., *PNAS*, 84:2708–2712 (1987).

The continuous FPTase activity assay is based on the enhancement of fluorescence and the accompanying shift to lower wavelength emission maximum of certain fluorophores, like dansyl, upon change from a polar to non-polar molecular environment (Lakowicz, *Principles of Fluorescence Spectroscopy*, Plenum Press, New York, (1983)). The present invention utilizes an acceptor peptide substrate with an environmentally sensitive fluorescence probe positioned proximally to the reaction center. Substrate pentapeptide N-dansyl-GlyCysValLeuSer(Ds Gly CysValLeuSer) (SEQ.ID.NO.1) and expected product N-dansyl-Gly(S-farnesyl-Cys)ValLeuSer(Ds-Gly[f-Cys]LeuSer) were synthesized by standard methods.

These peptides were synthesized using an ABI 401A synthesizer with standard t-Boc or Fmoc chemistry followed by acid cleavage. Crude peptides were purified by reverse phase (C18) HPLC (Brown, et al., *J. Am, Chem. Soc.*, 113, 3176–3177 (1991)). The purified peptide derivatives were characterized analytically. These peptides were characterized by high-resolution fast atom bombardment mass spectrometry and by $^1$HNMR.

Figure 1B:
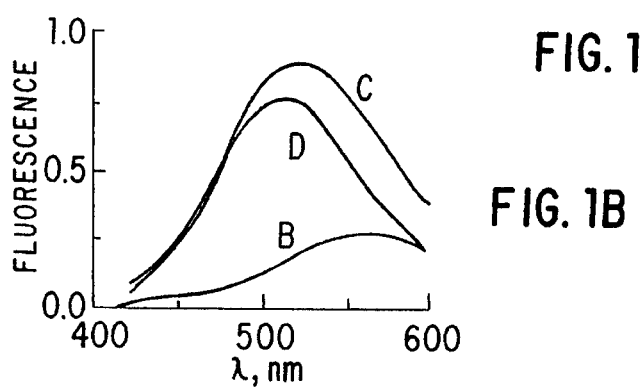

Incubation of Ds-GlyCysValLeuSer (SEQ.ID.NO.: 1 ) with recombinant human FPTase (hFPTase) and farnesyl diphosphate results in a time-dependent increase in fluorescence at 505 nm with excitation at 340 nm (FIG. 1). Covalent attachment of the farnesyl moiety to the cysteine thiol of Ds-GlyCysValLeuSer (SEQ.ID.NO.:1) places a non-polar, lipophilic group near to the dansyl moiety, altering the local chemical environment of the reporter group, and causing a dramatic change in its fluorescence properties. Fluorescence emission spectra taken before addition of enzyme and after complete conversion to product (FIG. 1B show a decrease of the emission maximum wavelength from 565 to 515 nm together with a 13-fold enhancement of fluorescence intensity at 505 nm (see difference curve D). Spectra of authentic product Ds-G[f-C]VLS and of product resulting from FPTase action (curve C) are superimposable.

Fluorescence enhancement and emission maximum shift depend upon the relative distance and chemical nature of the residue side chains between the cysteine group and the N-terminal dansyl group as well as upon the detergent content of the buffer. In addition, a number of other dansylated peptides (Ds-CysValIleMet (SEQ.ID.NO.:3), Ds-CysValLeuSer (SEQ.ID.NO.:4), Ds-LysCysValLeuSer (SEQ.ID.NO.:5), Ds-GlyCysCysValLeuSer (SEQ.ID.NO.:6), Ds-LysCysValLeuSer (SEQ.ID.NO:7)) were synthesized to optimize the sensitivity of the assay. Each of these peptides were substrates, and each peptide exhibited fluorescence enhancement.

Fluorescence is extremely sensitive to solvent conditions. For Example, reactions in Tris-HCl yielded higher fluorescence enhancements than in HEPES. The fluorescence of product compared to substrate increased with increasing detergent (octyl-$\beta$-D-glucopyranoside) content, up to a concentration of 0.6% (w/v). However, at concentrations above 0.2%, the enzyme activity appeared to decrease.

Using Ds-GlyCysValLeuSer (SEQ.ID.NO.:1) as substrate, FPTase follows Michaelis-Menten kinetics (FIG. 2), with the value of kcat(Ds-GlyCysValLeuSer=0.5 $S^{-1}$ (SEQ.ID.NO.: 1 ) and the value of $K_M$(Ds-GlyCysValLeuSer 1.4 $\mu$M (SEQ.ID.NO.:1). The value of $K_M$(FPP)= 30 nM in the presence of Ds-GlyCysValLeuSer (SEQ.ID.NO.:1) is the same as that determined previously using Ras as substrate (Pompliano, et al., *Biochemistry*, 31, 3800–3807 (1992)). The time-dependent change in fluorescence (reaction velocity) is linearly dependent upon enzyme concentration.

The assay of the instant invention can also be used to identify compounds which inhibit prenyl protein transferase activity or fatty acyl transferase activity, and in particular, farnesyl:protein transferase activity. For example, such an assay would comprise the steps of:

(a) reacting an acceptor peptide substrate, wherein the acceptor peptide substrate has a fluorescence probe positioned proximally to the reaction center, with farnesyl diphosphate in the presence of a substance having farnesyl:protein transferase activity in the presence of the test compound; and (b) detecting whether the farnesyl residue is incorporated into the protein or peptide substrate, in which the ability of the test compound to inhibit farnesyl:protein transferase activity is indicated by a decrease of the incorporation of the farnesyl residue into the protein or peptide substrate as compared to the amount of the farnesyl residue incorporated into the protein or peptide substrate in the absence of the test compound.

In an embodiment of the assay used to evaluate inhibitors of farnesyl:protein transferase the decrease of the incorporation of the farnesyl residue in the presence of the test compound is detected by a reduction in the enhancement of the fluorescence of the reaction when compared to the enhancement of the fluorescence of the reaction in the absence of the test compound.

Figure 2:
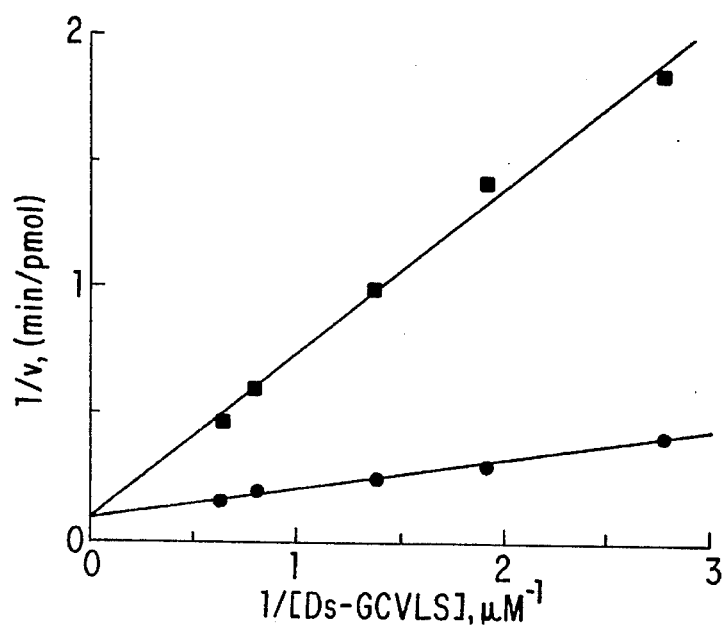
FIG. 2

Specifically, as a mimic of the normal Ras substrate, the dansylated peptides described herein, such as Ds-GlyCysValLeuSer (SEQ.ID.NO.:1) and the like, can be used to evaluate FPTase inhibitors as illustrated in FIG. 2. CysIlePheMet (SEQ.ID.NO.:2) is a competitive inhibitor of Ds-GlyCysValLeuSer (SEQ.ID.NO.:1) binding with a value of $K_i$(CysIlePheMet)=9 nM (SEQ.ID.NO.:2), which is similar to results found using Ras as acceptor substrate. (Pompliano, et al., *Biochemistry*, 31, 3800–3807 (1992)).

The present invention is illustrated according to the reaction scheme as set forth below:

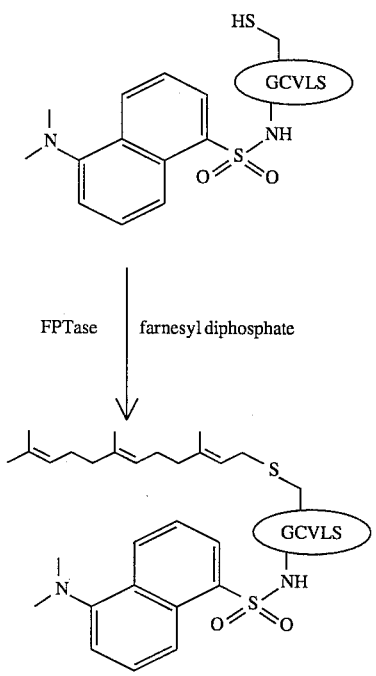

The invention is further defined by reference to the following examples, which are intended to be illustrative and not limiting. All temperatures are in degrees Celsius.

EXAMPLE 1

Preparation of N-dansyl-L-glycinyl-L-cysteinyl-L-valinyl-L-leucinyl-L-serine. (SEQ.ID.NO.:1)

N-dansyl GlyCysValLeuSer (SEQ.ID.NO.:1) was prepared by standard solid phase methods on an ABI 401A synthesiser using t-Boc methodology. Side chain ((4-Mebzl) cysteine and (bzl) serine) deprotection and cleavage of the dansylated peptide from the phenylacetamidomethyl resin was achieved by treatment with HF (12.5ml) in the presense of thiocresol and cresol (1 ml, 1:1 v/v) at 0° C. The crude peptide was purified by reverse phase ($C_{18}$) HPLC and lyophilized to afford a pale yellow solid (37.5 mg, 21% based on 0.2 mmol PAMt-Boc-L-serine (bzl)) $^1$H NMR (400 MHz, $CD_3OD$) δ 0.91 (3H, d, J=6.4 Hz) 0.93–0.98 (9H, m), 1.64 (2H, t, J=7.5 Hz) 1.71(1H, sept, 6.8 Hz), 2.10 (1H, sept, J=6.8 Hz), 2.69 (2H, br dd, J=6.0 and 2.5 Hz) 2.97 (6H, s), 3.59 (2H, s), 3.83 (1H, dd, J=11.4 and 4.0 Hz), 3.92 (1H, dd, J=11.3 and 4.5 Hz), 4.15 (1H, m), 4.45–4.55 (3H, m), 7.40 (1H, d, J= 7.5 Hz), 7.64 (1H, t, J= 8.8 Hz), 7.66 (1H, t, J= 9.0 Hz), 8.00 (1H, br d, J=8.0 Hz), 8.27 (1H, dd, J=7.3 and 1.3 Hz), 8.43 (1H, d, J=8.6 Hz), 8.58 (1H, d, J=8.4 Hz). High-resolution (+) FAB mass spectrum calcd. for $C_{31}H_{46}N_6O_9S_2$ (M+1): 711.2845 Found: 711.2832 Anal. Calcd. for $C_{31}H_{46}N_6O_9S_2 \cdot 1.6\ CF_3CO_2H$ C 45.98 H 5.37 N 9.41% Found C 45.95 H 5.02, N 9.58%

EXAMPLE 2

Preparation of N-dansyl S-farnesyl-L-glycinyl-L-cysteinyl-L-valinyl-L-leucinyl-L-serine.

To a stirred solution of N- dansyl GlyCysValLeuSer (15.3mg, $1.7 \times 10^{-5}$ mol) in dimethylformamide (0.8 ml), at room temperature under an atmosphere of argon, was added dropwise diisopropylethylamine (9.0 μd, $5.14 \times 10^{-5}$ mol), followed by farnesyl bromide (4.6ml, $1.7 \times 10^{-5}$ mol). After stirring for 1 hour at room temperature, the solvent was evaporated in vacuo and the crude product purified by reverse phase ($C_{18}$) HPLC and lyophilized to afford (11.0 mg, 62%) of a pale yellow solid. $^1$H NMR (300 MHz, $CD_3OD$) δ 0.85–1.00 (12H, m), 1.50–1.80 (3H, m), 1.59 (6H, s), 1.65 (6H, s), 1.90–2.20 (9H, m), 2.54 (1H, br dd, J=14.0 and 6.5 Hz), 2.72 (1H, br dd, J=14.0 and 6.5 Hz) 2.98 (6H, s) 3.14 (2H, d, J=8.0 Hz), 3.55 (2H, d, J=2.8 Hz), 3.80 (1H, br dd, J=11.4 and 3.8 Hz), 3.92 (1H, br dd, J=11.4 and 4.6 Hz), 4.16 (1H, t, J=6.8 Hz), 4.40–4.50 (3H, m), 5.03–5.15 (2H, m), 5.19 (1H, t, J=7.8 Hz), 7.41(1H, d, J= 7.4 Hz), 7.63 (1H, t, J= 7.5 Hz), 7.65 (1H, t, J= 7.5 Hz), 7.97 (2H, br d, J= 7.0 Hz), 8.12 (1H, d, J=8.3 Hz), 8.2.5 (1H, d, J=8.3 Hz), 8.42 (1H, d, J=8.4 Hz), 8.56 (1H, d, J=8.4 Hz). High-resolution (+) FAB mass spectrum calcd. for $C_{46}H_{70}N_6O_9S_2$ (M+1): 915.4724 Found: 915.4715 Anal. Calcd. for $C_{46}H_{70}N_6O_9S_2 \cdot CF_3CO_2H$ C 56.01, H 6.95, N 8.17% Found C 55.84, H 7.22, N 8.48%

---

What is claimed is:

1. An assay for determining prenyl:protein transferase activity, comprising:
   (a) reacting an acceptor peptide substrate, wherein the acceptor peptide substrate has a fluorescence probe positioned proximally to the reaction center, with a prenyl diphosphate in the presence of a substance suspected of having a corresponding prenyl:protein transferase activity; and
   (b) detecting whether the prenyl residue is incorporated into the peptide substrate, in which incorporation of the prenyl residue into the peptide substrate indicates prenyl:protein transferase activity and wherein the incorporation of the prenyl residue is detected by an enhancement of the fluorescence of the reaction.

2. The assay according to claim 1 wherein the prenyl:protein transferase activity is selected from farnesyl:protein transferase activity and geranylgeranyl:protein transferase activity.

3. An assay for determining farnesyl:protein transferase activity, comprising:
   (a) reacting an acceptor peptide substrate, wherein the acceptor peptide substrate has a fluorescence probe positioned proximally to the reaction center, with farnesyl diphosphate in the presence of a substance suspected of having farnesyl:protein transferase activity; and
   (b) detecting whether the farnesyl residue is incorporated into the peptide substrate, in which incorporation of the farnesyl residue into the peptide substrate indicates farnesyl:protein transferase activity and wherein the incorporation of the farnesyl residue is detected by an enhancement of the fluorescence of the reaction.

4. The assay according to claim 3 wherein the substance suspected of having farnesyl:protein activity is human FPTase.

5. The assay according to claim 3 for determining farnesyl:protein transferase activity, wherein the acceptor peptide substrate is selected from Ds-GlyCysValLeuSer (SEQ.ID.NO.: 1), Ds-CysValIleMet (SEQ.ID.NO.: 3), Ds-CysValLeuSer (SEQ.ID.NO.: 4), Ds-LysCysValLeuSer (SEQ.ID.NO.: 5), Ds-GlyLysCysValLeuSer (SEQ.ID.NO.: 6) and Ds-SerLysCysValLeuSer (SEQ.ID.NO.: 7).

6. An assay for identifying compounds that inhibit prenyl:protein transferase activity which comprises
   (a) reacting an acceptor peptide substrate, wherein the acceptor peptide substrate has a fluorescence probe positioned proximally to the reaction center, with a prenyl diphosphate in the presence of a substance having a corresponding prenyl:protein transferase activity in the presence of a test compound; and
   (b) detecting whether the prenyl residue is incorporated into the peptide substrate, in which the ability of the test compound to inhibit prenyl:protein transferase activity is indicated by a decrease of the incorporation of the prenyl residue into the peptide substrate as compared to the amount of the prenyl residue incorporated into the peptide substrate in the absence of the test compound and wherein the decrease of the incorporation of the prenyl residue in the presence of the test compound is detected by a reduction in the enhancement of the fluorescence of the reaction when compared to the enhancement of the fluorescence of the reaction in the absence of the test compound.

7. The assay according to claim 6 wherein the prenyl:protein transferase activity is selected from farnesyl:protein transferase activity and geranylgeranyl:protein transferase activity.

8. An assay for identifying compounds that inhibit farnesyl:protein transferase activity which comprises
   (a) reacting an acceptor peptide substrate, wherein the acceptor peptide substrate has a fluorescence probe positioned proximally to the reaction center, with farnesyl diphosphate in the presence of a substance having farnesyl:protein transferase activity in the presence of a test compound; and
   (b) detecting whether the farnesyl residue is incorporated into the peptide substrate, in which the ability of the test compound to inhibit farnesyl:protein transferase activity is indicated by a decrease of the incorporation of the farnesyl residue into the peptide substrate as compared to the amount of the farnesyl residue incorporated into the peptide substrate in the absence of the test compound and wherein the decrease of the incorporation of the prenyl residue in the presence of the test compound is detected by a reduction in the enhancement of the fluorescence of the reaction when compared to the enhancement of the fluorescence of the reaction in the absence, of the test compound.

9. An acceptor peptide substrate which is selected from Ds-GlyCysValLeuSer (SEQ.ID.NO.: 1 ), Ds-CysValIleMet (SEQ.ID.NO.: 3), Ds-CysValLeuSer (SEQ.ID.NO.: 4), Ds-LysCysValLeuSer (SEQ.ID.NO.: 5), Ds-GlyLysCysValLeuSer (SEQ.ID.NO: 6) and Ds-SerLysCysValLeuSer (SEQ.ID.NO.: 7).

\* \* \* \* \*

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Gly  Cys  Val  Leu  Ser
    1                        5

( 2 ) INFORMATION FOR SEQ ID NO:2:

（ i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

Cys Ile Phe Met
1

( 2 ) INFORMATION FOR SEQ ID NO:3:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:3:

Cys Val Ile Met
1

( 2 ) INFORMATION FOR SEQ ID NO:4:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:4:

Cys Val Leu Ser
1

( 2 ) INFORMATION FOR SEQ ID NO:5:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:5:

Lys Cys Val Leu Ser
1               5

( 2 ) INFORMATION FOR SEQ ID NO:6:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:6:

Gly Lys Cys Val Leu Ser
1               5

( 2 ) INFORMATION FOR SEQ ID NO:7:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:7:

Ser Lys Cys Val Leu Ser
1               5